United States Patent
Zedell et al.

(10) Patent No.: US 11,282,114 B2
(45) Date of Patent: *Mar. 22, 2022

(54) TARGETED CONTENT PAGE GENERATION

(71) Applicant: Under Armour, Inc., Baltimore, MD (US)

(72) Inventors: Jeremy Zedell, Austin, TX (US);
Murtaza Ali, Baltimore, MD (US);
Ralph Marczynski, Austin, TX (US);
Mary Lawyer, Baltimore, MD (US);
Ken Valencik, Baltimore, MD (US);
Sid Jatia, Austin, TX (US); Barbra Sainsurin, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/075,033

(22) Filed: Oct. 20, 2020

(65) Prior Publication Data
US 2021/0209649 A1     Jul. 8, 2021

Related U.S. Application Data

(63) Continuation of application No. 15/191,944, filed on Jun. 24, 2016, now Pat. No. 10,817,909.

(51) Int. Cl.
*G06Q 30/00* (2012.01)
*G06Q 30/02* (2012.01)
*H04M 1/72403* (2021.01)
*H04L 67/306* (2022.01)
*A61B 5/0205* (2006.01)
(Continued)

(52) U.S. Cl.
CPC ..... *G06Q 30/0269* (2013.01); *G06Q 30/0255* (2013.01); *H04M 1/72403* (2021.01); *A61B 5/0022* (2013.01); *A61B 5/0205* (2013.01); *A61B 5/02438* (2013.01); *A61B 5/1112* (2013.01); *A61B 5/1118* (2013.01); *A61B 5/486* (2013.01); *A61B 5/4806* (2013.01);
(Continued)

(58) Field of Classification Search
None
See application file for complete search history.

(56) References Cited

U.S. PATENT DOCUMENTS 8,533,620 B2    9/2013  Hoffman
8,652,010 B2    2/2014  Ellis
(Continued)

OTHER PUBLICATIONS

Su et al., "Activity recognition with smartphone sensors", Jun. 3, 2014, Tsinghua Science and Technology, ISSN 1007-0214 02/11 pp. 235-249 (Year: 2014).*

(Continued)

*Primary Examiner* — Naresh Vig
(74) *Attorney, Agent, or Firm* — Maginot, Moore & Beck LLP

(57) ABSTRACT

A method of operating a health tracking system includes utilizing user profile data for a user and health parameter data received from a health tracking device associated with the user to derive parameters relating to the user. The parameters are compared to tags associated with content pages or objects to determine a relevancy or match. Particular ones of a plurality of content pages or objects are selected for delivery to the user based on the comparison.

19 Claims, 12 Drawing Sheets

(51) Int. Cl.
  *A61B 5/00* (2006.01)
  *A61B 5/024* (2006.01)
  *A61B 5/11* (2006.01)

(52) U.S. Cl.
  CPC ........... *A61B 5/4866* (2013.01); *A61B 5/6898* (2013.01); *H04L 67/306* (2013.01)

(56) References Cited

U.S. PATENT DOCUMENTS

| | | |
|---|---|---|
| 8,801,577 B2 | 8/2014 | Dibenedetto |
| 8,814,755 B2 | 8/2014 | Ellis |
| 8,892,999 B2 | 11/2014 | Nims |
| 8,894,548 B2 | 11/2014 | Ellis |
| 9,940,682 B2 | 4/2018 | Hoffman |
| 10,497,022 B2 | 12/2019 | Carlson |
| 2007/0179356 A1 | 8/2007 | Wessel |
| 2010/0185398 A1 | 7/2010 | Berns |
| 2011/0028160 A1 | 2/2011 | Roeding |
| 2011/0066479 A1 | 3/2011 | Benson |
| 2011/0072457 A1 | 3/2011 | Lanfermann |
| 2012/0240080 A1 | 9/2012 | O'Malley |
| 2013/0151343 A1 | 6/2013 | Phan |
| 2013/0211852 A1 | 8/2013 | Roizen |
| 2013/0282155 A1 | 10/2013 | Li |
| 2013/0332286 A1* | 12/2013 | Medelius ........... G06Q 30/0269 705/14.66 |
| 2014/0006129 A1 | 1/2014 | Heath |
| 2015/0066173 A1 | 3/2015 | Ellis |
| 2015/0105883 A1 | 4/2015 | Ellis |
| 2015/0105884 A1 | 4/2015 | Ellis |
| 2015/0141202 A1 | 5/2015 | Ellis |
| 2015/0200878 A1 | 7/2015 | Shih |
| 2015/0238817 A1 | 8/2015 | Watterson |
| 2015/0248844 A1 | 9/2015 | Ellis |
| 2015/0258372 A1 | 9/2015 | Tagliabue |
| 2016/0078493 A1 | 3/2016 | Liberty |
| 2016/0345874 A1 | 12/2016 | Raisoni |
| 2020/0161838 A1 | 5/2020 | Hoffman |

OTHER PUBLICATIONS

Map My Walk by Under Armour, 2011, Under Armour, Inc., software released through itunes.apple.com (2011).
Bodana, Rahul, Map My Walk by Under Armour App for Android, iOS download Review & Troubleshooting, Dec. 21, 2017, https://apptircker.in (2017).

* cited by examiner

400

- 410 — Obtain user profile data for a user of a health tracking system.
- 420 — Receive user health data from a health tracking device.
- 430 — Determine personal shopping parameters for the user.
- 440 — Prepare targeted pages.
- 450 — Select one or more targeted pages for presentation to the user.
- 460 — Send the selected at least one of the plurality of targeted pages to a user display device.

FIG. 4

TARGETED CONTENT PAGE GENERATION

CROSS-REFERENCE TO RELATED APPLICATIONS

This application is a continuation of U.S. patent application Ser. No. 15/191,944, filed Jun. 24, 2016, and entitled "Targeted Content Page Generation," the contents of which are incorporated herein by reference in their entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The method and system disclosed in this document relate to content page presentation and, more particularly, to devices configured to collect health and fitness information relating to a user and the use of such information to display product information to the user.

BACKGROUND

Health and fitness tracking devices are increasingly utilized by individuals interested in tracking metrics and other health data related to their personal health and fitness. The health data collected by health tracking devices is typically processed and stored by the associated health tracking system and then used to provide health data to the user. The health data may be used to provide the user with individualized information related to athletic performance over time, goal achievement, average biometric statistics, total calorie consumption, and any of various other types of health data. The user health data collected and processed by the health tracking system may also be used by a system administrator to perform demographic analysis or some related group analysis, and this data may then be available for viewing by each user of the health tracking system.

In view of the foregoing, it would be advantageous to offer improved services to the users of a health tracking system. It would be advantageous if such a health tracking system were capable of using health tracking data to offer individualized services including content pages for each user.

SUMMARY

In accordance with one exemplary embodiment of the disclosure, there is provided a method of operating a health tracking system. The method comprises obtaining user profile data for a user and receiving health parameter data from a health tracking device associated with the user. The health parameter data may be obtained by a sensor and/or manually entered by the user. The method further comprises determining one or more personal shopping parameters for a user based at least in part on the user profile data and the health parameter data. After the personal shopping parameters for the user are determined, the method includes selecting at least one of a plurality of targeted content pages, each of the plurality of targeted content pages associated with one or more descriptive tags. Selection of the at least one of the plurality of targeted content pages is based at least in part on the one or more personal shopping parameters for the user and the one or more descriptive tags associated with each of the plurality of targeted content pages. The method further includes providing the selected at least one of the plurality of targeted content pages to a display device.

Pursuant to another exemplary embodiment of the disclosure, there is provided a method of presenting products for purchase on a display device. The method comprises determining one or more user specific parameters as well as generating a plurality of targeted content pages. Each of the plurality of targeted content pages includes a narrative portion and a product portion. Each of the plurality of narrative targeted content pages is associated with one or more descriptive identifiers. At least one of the plurality of targeted content pages is selected based at least in part on a similarity between the one or more user specific parameters and the one or more descriptive identifiers associated with each of the plurality of targeted content pages. The method further comprises sending the selected at least one of the plurality of targeted content pages to the display device.

In accordance with yet another exemplary embodiment of the disclosure, there is provided a method of operating a health tracking system. The method includes generating a user profile comprising data relating to a user and receiving health parameter data from a health tracking device. The health parameter data may be obtained by a sensor and/or manually entered by the user. The method further comprises determining one or more aspects relating to the user based at least in part on the health parameter data. Purchase options for the user are selected based on the determined one or more aspects relating to the user. The selected purchase options are sent to a user display device.

The above described features and advantages, as well as others, will become more readily apparent to those of ordinary skill in the art by reference to the following detailed description and accompanying drawings. While it would be desirable to provide a health tracking system that provides one or more of these or other advantageous features, the teachings disclosed herein extend to those embodiments which fall within the scope of the appended claims, regardless of whether they accomplish one or more of the above-mentioned advantageous features.

BRIEF DESCRIPTION OF THE DRAWINGS

The foregoing aspects and other features of a health and fitness tracking system are explained in the following description, taken in connection with the accompanying drawings.

FIG. 4 is a logical flow diagram illustrating an exemplary method for operating the health tracking system of FIG. 1;

Figure 1:
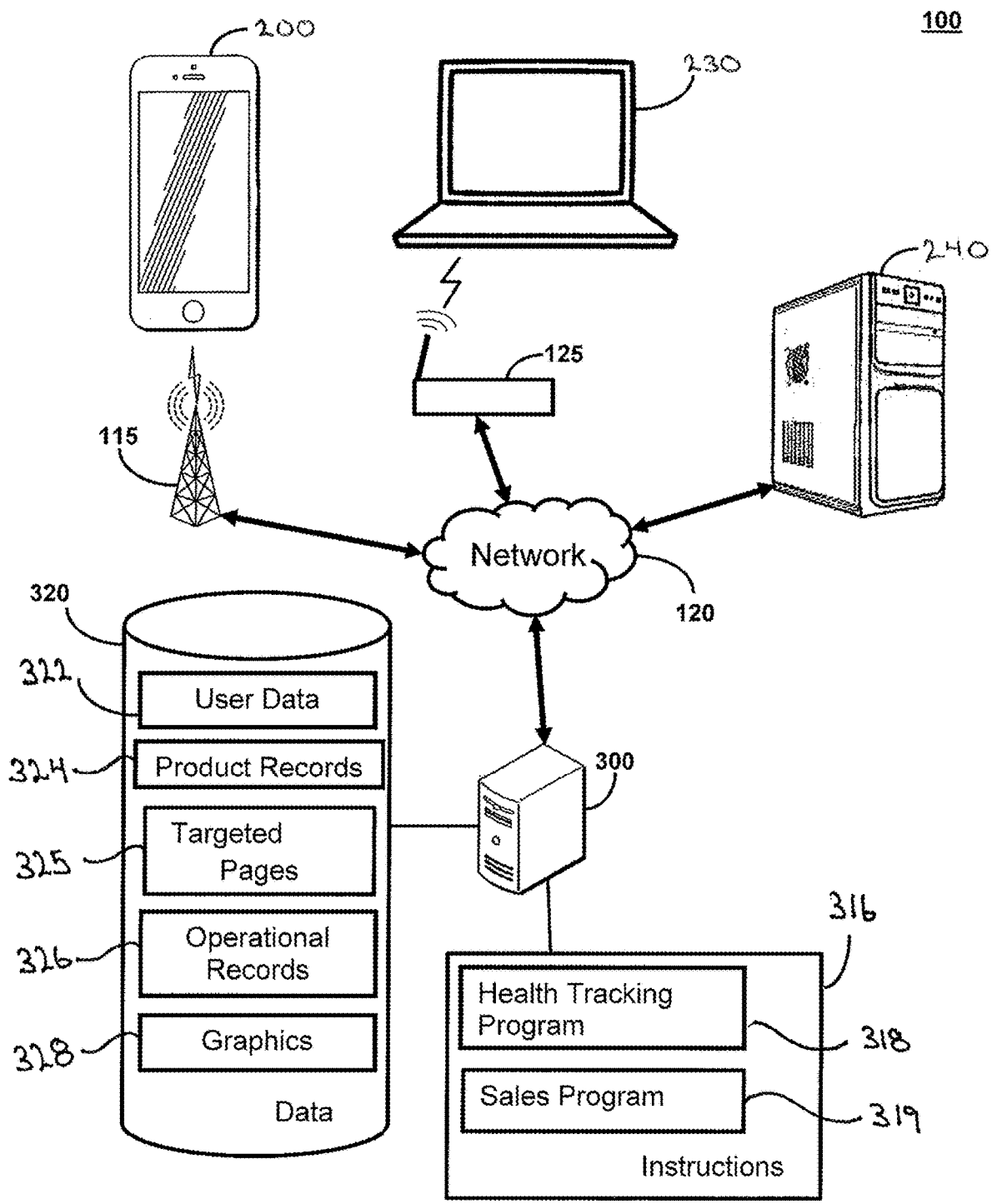
FIG. 1 is a block diagram illustrating an exemplary health tracking system.

All Figures © Under Armour, Inc. 2016. All rights reserved.

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

Disclosed embodiments include a method, system, and computer readable medium associated with providing targeted content pages to a user based at least in part on data collected via one or more health tracking applications.

In the following detailed description, reference is made to the accompanying drawings which form a part hereof wherein like numerals designate like parts throughout, and in which is shown, by way of illustration, embodiments that may be practiced. It is to be understood that other embodiments may be utilized and that structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Health Tracking System

With reference to FIG. 1, an exemplary embodiment of a health tracking system 100 for providing targeted page generation is shown. In the illustrated embodiment, the health tracking system 100 includes a plurality of health tracking devices in communication with a system server 300 or other data processing system over a network 120 such as, e.g., the Internet. The health and fitness tracking devices (which may also be referred to herein as "health tracking devices") comprise any computerized apparatus which includes a user interface and is configured to obtain, measure, sense or otherwise receive health related parameter data. Exemplary health tracking apparatus include, e.g., a personal electronic device (not shown), a smartphone 200, a laptop computer 230, a tablet computer, and/or a desktop computer 240, however it is appreciated that others may be utilized with equal success.

In at least one embodiment, the user interface may comprise an LCD touch screen or the like, a mouse or other pointing device, a keyboard or other keypad, speakers, and/or a microphone, as will be recognized by those of ordinary skill in the art. The user interface provides the user with access any of various health, fitness and activity related data such as food and nutritional consumption, calorie expenditure, heart rate, distance travelled, steps taken, etc.

Health tracking devices (including the exemplary devices discussed above) may obtain data which is collected via one or more sensors associated to or in communication with the health tracking device, such as heart rate monitors, step counters, stair counters, global positioning system ("GPS") tracking devices, scales, sleep monitors, as well as various other motion tracking and/or biometric monitoring devices. Sensors allow the user to easily track and automatically log activity information with the health tracking device. Alternatively, or in addition to the user of sensors, a user may manually enter health related data in the health tracking devices. The term "health tracking system" as used herein refers to a health tracking system and/or health and fitness tracking system which includes or is associated with one or more health tracking devices, wherein each health tracking device may or may not be used in association with a sensor device. In another embodiment, the health tracking device may itself comprise a sensor device capable of generating health parameter data. The term "health parameter data" as used herein (which may also be referred to herein as "health data") refers to any of various different health and fitness metrics associated with the user, such as steps taken, stairs climbed, distance travelled, heart rate, calories consumed, food consumed, calories spent, breathing rate, as well as any of various other health and fitness information that may be collected by a sensor (at a sensor device and/or health tracking device) or manually entered by the user.

The server 300 comprises computerized device configured to run one or more software applications on a processor thereof. The server 300 of the present embodiment is further configured to receive user health data entered or otherwise obtained at the health tracking devices and store such user health data records in a storage apparatus. Alternatively, the server 300 may be in communication with a separate storage entity (not shown) for storage thereof. As is explained in further detail below with respect to FIG. 3, the storage apparatus may include both program instructions 316 and data 320. The program instructions include a health tracking program 318 and a sales program 319. The data 320 includes user data 322, product data 324, targeted content pages 325, operational records 326, and graphics 328.

In another embodiment (not shown), a user activity database and a user profile database may be provided. The user activity database comprises one or more data stores which is configured to house information relating to the recorded activity of one or more users. In one embodiment, the user activity database stores raw data having one or more identifiers associated thereto. The identifiers provide information which associates the data to e.g., a particular workout (such as by date/time), a particular user profile, a particular user device, and in some instances, to one or more particular locations (such as via additional geopositioning data). The user profile database comprises one or more data stores which is configured to house user specific information including the user's contact information (e.g., email, geographic location, etc.), physiological parameters (e.g., gender, identity, weight, height, etc.), particular preferences (sports, celebrities/athletes, etc. of interest), goals, and other information relating to each registered user. Information specific to individual ones of a plurality of users is uniquely identified within the user activity database and the user profile database via a unique user profile identifier, user device identifier, or other unique identifier.

The health tracking devices (including the exemplary devices discussed above) are configured to communicate with the system server 300. Accordingly, the health tracking devices send user health data to the system server 300 for storage thereof; and in one embodiment, may further receive processed data from the system server 300. In another embodiment, the foregoing functions are performed via execution of one or more software applications at the server 300 in communication with one or more complementary software applications at the health tracking devices. For example, a back-end health tracking program 318, running on the processor of the sever 300 may be utilized to accomplish the foregoing, as explained in further detail below. A related client-side software application for performing the same is also utilized on the health tracking devices.

Health Tracking Device

As noted above, the health tracking devices may be provided in any of various forms. Examples of a health tracking devices configured for use with the health tracking system 100 include a smartphone 200, a laptop computer 230, and a desktop computer 240, as shown in FIG. 1. Accordingly, it will be recognized that the health tracking devices may comprise portable electronic devices such as the smartphone 200 or the laptop computer 230, or stationary electronic devices such as the desktop computer 240. Other examples of health tracking devices include, handheld or tablet computers, smart watches, portable media players, other wearable devices (including health parameter sensors), wearable heart rate monitors or bands, or any of various other health tracking devices configured to receive health data (not shown).

In one embodiment, data entered at one health tracking device may be provided to other ones of the user's devices (including additional health tracking devices). For example, health parameter data entered at the smart phone 200 may be provided to the desktop computer 240 and/or the laptop computer 230 for storage thereat; in another example, data collected at a heart rate monitor device may be provided to the user's smartphone. Alternatively, the data may be stored at a single network storage apparatus (not shown) having a dedicated portion of storage for health parameter records relating to the user and accessible by all of the user's devices. As shown in FIG. 1, in order to connect to the network 120, the health tracking devices are generally configured to utilize any of various wired or wireless communications components, infrastructures and systems, such as cell towers 115 of a mobile telephony network, wireless routers 125, Bluetooth®, near field communication (NFC), or physical cables.

Figure 2:
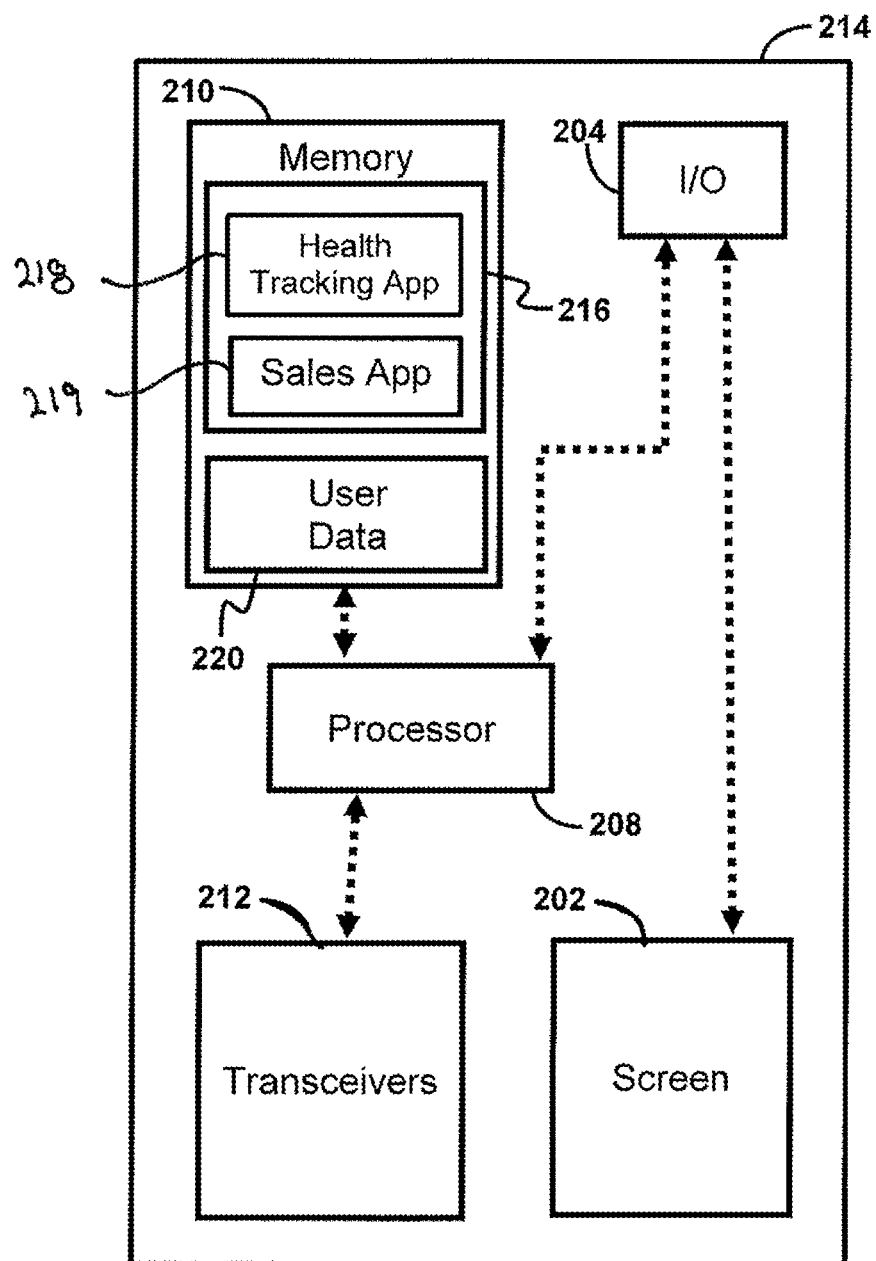
FIG. 2 is a block diagram illustrating an exemplary smartphone of the health tracking system of FIG. 1.

With reference now to FIG. 2, in at least one embodiment a health tracking device is provided in the form of a smartphone 200. The smartphone 200 includes a display screen 202, an input/output (I/O) interface 204, a processor 208, a memory 210, and one or more transceivers 212. The smartphone 200 also includes a protective outer shell or housing 214 designed to retain and protect the electronic components positioned within the housing 214. The smartphone 200 also includes a battery (not shown) configured to power the display screen 202, processor 208, transceivers 212 and various other the electronic components within the smartphone 200.

The display screen 202 of the smartphone 200 may be an LCD screen or any of various other screens appropriate for the personal electronic device. The I/O interface 204 of the smartphone 200 includes software and hardware configured to facilitate communications with the user. The I/O interface 204 is connected to the display screen 202 and is configured to visually display graphics, text, and other data to the user using the display screen 202. As will be recognized by those of ordinary skill in the art, the components of the health tracking device may vary depending on the specific type of device used. Alternative health tracking devices, such as the laptop 230 and the desktop 240, may include much of the same functionality and components as the smartphone 200 shown in FIG. 2, but may not include all the same functionality or components and/or may include additional components necessary for functionality thereof.

The processor 208 of the smartphone 200 may be any of various processors as will be recognized by those of ordinary skill in the art. The processor 208 is connected to the I/O interface 204, the memory 210, and the transceivers 212, and is configured to deliver data to and receive data from each of these components. The memory 210 is configured to store information, including user data 220 and instructions 216 for execution by the processor 208. It will be recognized by those of ordinary skill in the art that a "processor" includes any hardware system, hardware mechanism or hardware component that processes data, signals or other information. A processor can include a system with a central processing unit, multiple processing units, dedicated circuitry for achieving functionality, or other systems.

The transceivers 212 may be any of various transceivers configured for communication with other electronic devices, including the ability to send communication signals and receive communication signals. The transceivers 212 may include different types of transceivers configured to communicate with different networks and systems. Such transceivers are well known and will be recognized by those of ordinary skill in the art. In some exemplary embodiments, the transceivers 212 include a transceiver configured to allow the smartphone 200 to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In other exemplary embodiments, the transceivers 212 include a transceiver configured to allow the smartphone 200 to communicate with any of various local area networks using WiFi, Bluetooth® or any of various other communications schemes.

With continued reference to FIG. 2, the memory 210 includes program instructions 216 and user data 220. The program instructions 216 include a health tracking application 218 and a sales application 219. The health tracking application 218 includes program instructions for receiving and transmitting user health data, and also program instructions for a graphical user interface configured to provide a client-side health tracking application. The health tracking application 218 on the smartphone 200 is associated with the back-end (or network-side) health tracking program 318 on the server 300. The sales application 219 includes program instructions for presenting products for sale and receiving product orders from the user, and also program instructions for providing a graphical user interface, as explained in further detail below. The product sales application 219 is associated with the back-end sales program 319 on the server 300.

In another embodiment, the smartphone 200 may be further configured to run a processing application configured to receive a plurality of content cards from a first entity and instructions for the display of the cards from a second entity. The processing application is configured to use the instructions to put together one or more content pages as discussed herein. In one variant, various cards may be utilized to form a single content page or series of pages, the layout, order, size, etc. of the cards being mandated by the instructions.

The memory 210 may further be configured to store certain user data 220, including user profile data and health parameter data. The user profile data is data that identifies the user and various user demographics within the health tracking system 100. The user profile data may include, e.g., user gender, height, weight, user identifier, password, normalized vital statistics, health conditions, favorite or preferred sports, favorite or preferred athletes, etc. The user typically enters the user profile data manually when registering to use the health tracking system 100. Alternatively, certain data may be obtained passively by one or more sensors in communication with the user device 200 (such as e.g., height, weight, etc.).

The user data 220 also includes health parameter data (which may also be referred to herein as "user health data"). The health parameter data is data related to various activities of the user, including health and fitness activities, water, drug, and nutrition consumption information, and/or any of various other health-related activities. The user health data may be collected from one or more sensors associated with the user and/or may be manually entered by the user into the smartphone 200 or other device in communication therewith. Examples of user health data include steps taken, stairs climbed, distance travelled, type of activity performed (e.g., running, weightlifting, golf, basketball, etc.), heart rate, calories or food consumed, water consumed, calories spent, breathing rate, time spent sleeping, as well as any of various other health and fitness information.

The processor 208 is configured to read the program instructions 216 from the memory 210 and execute the program instructions to provide the health tracking application 218 to the user for the purpose of performing health and fitness related tasks for the user, including receiving, displaying, modifying, analyzing, and transmitting the user data 220. Further operations of the health tracking application 218 are described in further detail below. The processor 208 is also configured to read the program instructions 216 from the memory 210 and execute the program instructions to provide the sales application 219 to the user so for the purpose of offering products for purchase by the user. In one embodiment, this includes receiving instructions from a server-side entity which provide parameters for building individual content pages and receiving objects (such as text, images, audio/video, etc.) from another server-side entity which are selected based on the instructions for inclusion in the content pages. Operations of the sales application 219 are described in further detail below.

The memory 210 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. In at least one embodiment, the software (such as, e.g., the client side health tracking program 218 and the sales application 219) may be downloaded from a network location, such as via the Internet, and installed in the memory 210.

A computer program product implementing an embodiment disclosed herein may therefore comprise one or more computer-readable storage media storing computer instructions translatable by a processor to provide an embodiment of a system or perform an embodiment of a method disclosed herein (see e.g., FIG. 4). Computer instructions may be provided by lines of code in any of various languages as will be recognized by those of ordinary skill in the art. A "non-transient computer-readable medium" may be any type of data storage medium that can store computer instructions, including, but not limited to the memory devices discussed above.

System Server

Figure 3:
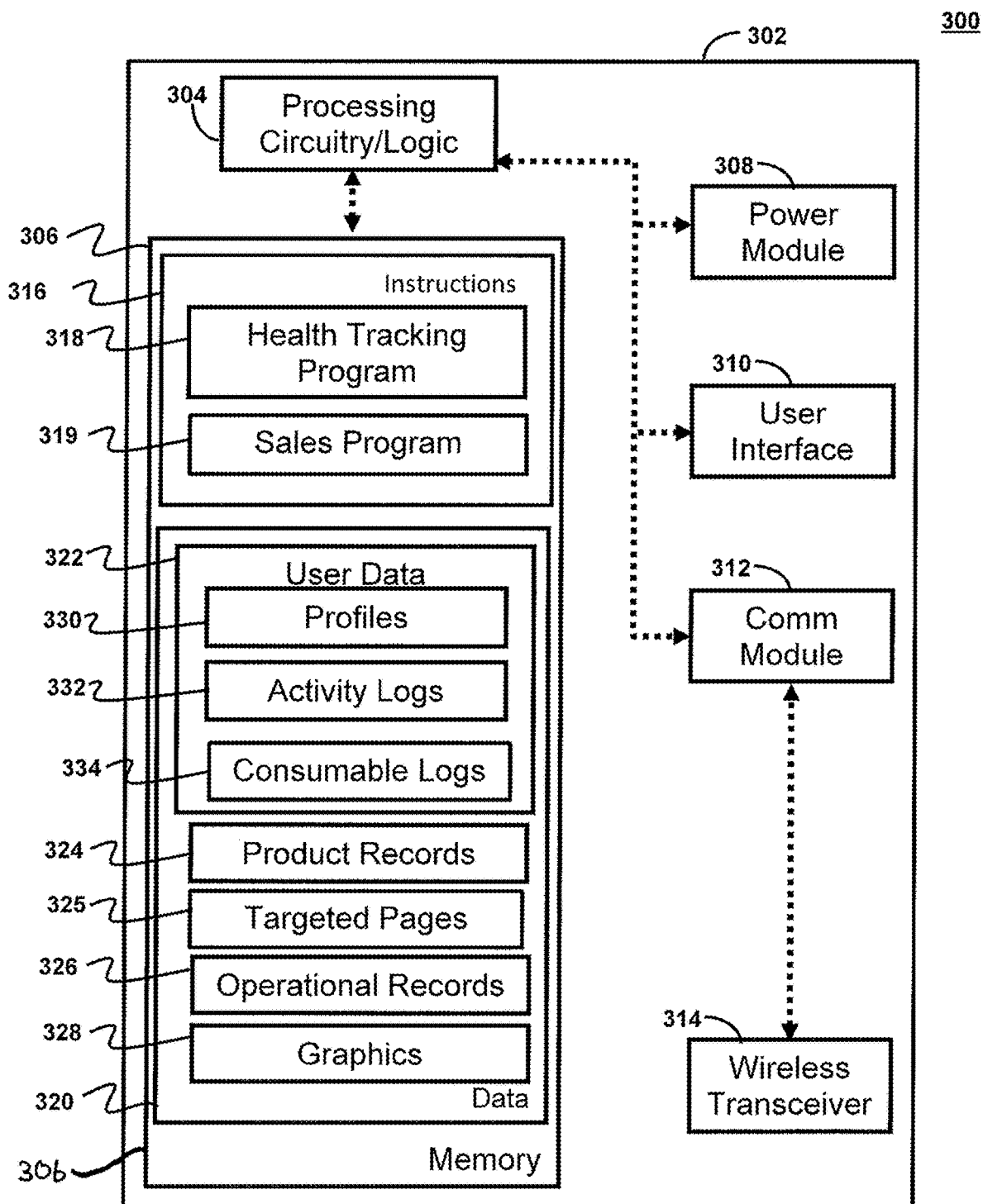
FIG. 3 is a block diagram illustrating an exemplary system server or data processing system of the health tracking system of FIG. 1.

With reference now to FIG. 3, a block diagram of an exemplary embodiment of the system server 300 of FIG. 1 is shown. It should be appreciated that the embodiment of the system server 300 shown in FIG. 3 is only one exemplary embodiment of a system server 300. As such, the exemplary embodiment of the system server 300 of FIG. 3 is merely representative of any of various manners or configurations of system servers or other data processing systems that are operative in the manner set forth herein.

The system server 300 of FIG. 3 is typically provided in a housing, cabinet or the like 302 that is configured in a typical manner for a server or related computing device. The system server 300 includes one or more of: processing circuitry/logic 304, memory 306, a power module 308, a user interface 310, a network communications module 312, and a transceiver 314.

The processing circuitry/logic 304 is operative, configured and/or adapted to operate the system server 300 including the features, functionality, characteristics and/or the like as described herein. To this end, the processing circuitry/logic 304 is operably connected to the memory 306, the power module 308, the user interface 310, the network communications module 312, and the wireless transceiver 314. The memory 306 is configured to store network-side instructions 316 as well as data 320. The instructions 316 include a health tracking program 318 and a sales program 319 for execution by the processing circuitry/logic 304. The data 320 in the memory 306 is configured for use by the health tracking health tracking program 318 and the sales program 319. The data 320 includes user data 322, product records 324, targeted content pages 325, operational records 326, and graphics 328. As discussed in greater detail below, the health tracking program 318 and the sales program 319 are configured to provide targeted content page functionality to the user based on the data 320 stored in the memory 306.

With continued reference to FIG. 3, the power module 308 of the system server 300 is operative, adapted and/or configured to supply appropriate electricity to the system server 300 (i.e., including the various components of the system server 300). The power module 308 may operate on standard 120 volt AC electricity, but may alternatively operate on other AC voltages or include DC power supplied by a battery or batteries.

The network communication module 312 of the system server 300 provides an interface that allows for communication between the server 300 and any of various devices. In particular, the network communications module 312 includes a local area network port that allows for communication with any of various local computers housed in the same or nearby facility. In some embodiments, the network communications module 312 further includes a wide area network port that allows for communications with remote computers over the Internet (e.g., network 120 of FIG. 1). Alternatively, the system server 300 communicates with the network 120 via a modem and/or router of the local area network. In one embodiment, the network communications module is equipped with a Wi-Fi transceiver 314 or other wireless communications device. Accordingly, it will be appreciated that communications with the system server 300 may occur via wired communications or via the wireless communications. Communications may be accomplished using any of various known communications protocols. In the embodiment of FIG. 3, the wireless transceiver 314 is identified as a Wi-Fi transceiver, but it will be recognized that the wireless transceiver may use a different communications protocol.

The user interface 310 allows the system server 300 to be accessed locally by an authorized user (i.e., an administrator or operator). In at least one embodiment, the user interface 310 may suitably include an LCD touch screen or the like, a mouse or other pointing device, a keyboard or other keypad, speakers, and a microphone, as will be recognized by those of ordinary skill in the art. Accordingly, the user interface 310 is configured to provide an administrator or other authorized user with access to the memory 306 and allow the authorized user to amend, manipulate and display information contained within the memory 306.

As mentioned above, the memory 306 includes various programs and other instructions that may be executed by the processor circuitry/logic 304. In particular, the memory 306 of the system server 300 of FIG. 3 includes the health tracking program 318 and the sales program 319. The health tracking program 318 is configured to cause the system server 300 to enable a user to enter health parameter data using a health tracking device 110 associated with the user and/or receive health parameter data from one or more sensors. Such health data is stored in the activity logs 332 or the consumable logs 334. Execution of the health tracking program 318 by the processor circuitry/logic 304 results in health data and other signals being sent to and received from the server 300 to the health tracking device via the communications module 312. The health tracking program 318 is further configured to deliver the graphics 328 to be displayed as various graphical views and screen arrangements on the health tracking device of the user. Alternatively, the foregoing graphics displays are preloaded at the user device (such as the smart phone 200) and accessed thereby without network-side assistance or with minimal network-side assistance.

The sales program 319 is configured to utilize the health parameter data received from one or more health tracking devices to provide data from the product records 324 to the user. As described in further detail below, each of the product records 324 is associated with one or more targeted content pages 325 that provide purchase options for the user. The targeted content pages are sent to the user for display on the screen of the user's health tracking device. Accordingly, the sales program 319 is configured to deliver the graphics 328 to be displayed as various graphical views and screen arrangements on the health tracking device of the user. Alternatively, the foregoing graphics displays are preloaded at the user device (such as the smart phone 200) and accessed thereby without network-side assistance or with minimal network-side assistance. Various aspects of the targeted content pages 325 and product records 324 are explained in further detail below in association with operation of the sales program 319.

While the sales program 319 and the health tracking program 318 have been described with reference to FIG. 3 as two separate programs within the instructions 316 included in the memory 306, it will be recognized that in at least one embodiment, the sales program 319 and the health tracking program 318 may comprise a single program. Alternatively, the sales program 319 and the health tracking program 318 may be maintained as distinct components of two separate systems wherein the health tracking program 318 is provided on a first server at a first location and the sales program 319 is provided on a second server at a second location that is remote from the first location. In such embodiments, the sales program 319 may utilize any number of APIs to access the data in the remote databases of the health tracking system 100 and incorporate such information for use by the sales program 319.

With continued reference to FIG. 3, the user data 322 includes a plurality of user profiles 330 and corresponding health data in the form of activity logs 332 and consumable logs 334. The user profiles 330 include profile data for each user of the health tracking system 100. Each user profile 330 includes demographic information for the users such as name, age, gender, height, weight, performance level (e.g., beginner, intermediate, professional, etc.), and/or other identification information for the user. In at least one embodiment, the user profile data may also include personal shopping parameters relating to the user, as explained in further detail below.

The user data also includes health parameter data associated with each user. In at least one embodiment, the health parameter data includes at least one an activity log 332 and/or consumable log 334 for each user. The activity log 332 allows the user to track activity such as sleep, workouts and other fitness activity that the user performed over a period of days, and any metrics associated to such activity. For example, the activity log 332 may allow the user to enter steps taken, distance travelled, heart rate, calories spent, time and duration of activity (including sleep), or other data related to one or more workouts or other physical activity. In some embodiments, the health parameter data used to create the records in the activity log 332 is collected by sensors (not shown) associated with the health tracking devices. Exemplary sensors include heart rate sensors, step counters, timers, GPS devices, etc. Alternatively, or in addition to the sensors, other health data may be manually entered by the user in order to create one or more records in the activity logs 332. Further, the health data may further processed by the health tracking device and/or the server 300 to create additional health parameter data in the activity logs 332. For example, health data sensed by various sensors may be processed to create a perceived exertion level or score for the user during an activity. In another example, health parameter data may be generated from raw data collected by the sensors, such as GPS data being utilized to determine a distance of a user's run, walk, jog, etc.

The consumable log 334 allows the user to track health data in the form of consumables that are consumed by the user over a period of days and any nutritional data associated with the food consumed. For example, the consumable log may allow the user to enter particular consumable that is consumed by the user and keep track of the associated calories, macronutrients, sugar, carbohydrates, protein, or any of various other nutritional data associated with the consumables entered by the user in the consumable log. In this manner, the consumable log provides a sort of diary or record of consumables consumed by the user over a period of time.

With continued reference to FIG. 3, the product records 324 include entries for various products offered for sale via the health tracking program 318. In at least one embodiment, the products offered for sale include sportswear and sporting goods such as, e.g., shoes, cleats, shirts, pants, socks hats, headgear, pads, balls, health and fitness sensors, etc. Each product record includes a number of fields or tags that describe some attribute, feature, or other identifying information related to the product for sale. Such attribute, features and other identifying information for a product may also be referred to herein as a "facet" of the product (or a "product facet"). Examples of fields that describe product facets include the following: an identification string field that provides a textual description of the product (e.g., "running shoes", "T-shirt," "jacket," etc.); an identification code or part number (e.g., "MGS134X2016," etc.); a size (e.g., "6", "8," "10," "small," "medium," "large," "youth," "adult," etc.); a gender (e.g., "men's," "women's," "unisex," etc.); a color (e.g., "blue," "black," "red," etc.); a sport (e.g., "basketball," "running," "golf," "football," "volleyball," "baseball," "hunting," etc.); and any number of additional fields that may be appropriate for identifying the product (e.g., sleeve length, fabric type, pattern, materials, celebrity endorsement, sale price, etc.). Accordingly, each product record identifies a unique product for sale via the sales program 319. It will be recognized that in various embodiments, the fields of the product records may be configured differently such that a number of records are combined into a single record based on combined fields. For example, in at least one embodiment, the field may not represent a single size associated with the record, but a range of available sizes (e.g., "4-14," "S-XXL," etc.). Therefore, it will be recognized that the foregoing examples are merely illustrative of the information that may be provided in the product records 324.

The plurality of targeted content pages 325 in the data 320 of the memory 306 include content pages associated with one or more of the product records 324 and associated purchase options for the user. Each of the targeted content pages 325 includes a plurality of content page tags that may be used to associate the targeted content page with a user, as explained in further detail below. In at least one embodiment, the content page tags may be the same as or similar to product facets and/or personal shopping parameters of a user. For example, a first targeted content page may include the content page tags "golf," and "shirt," and "men's," and these content page tags may be the same as or similar to the product facets for one or more products. These content page tags may also be the same as or similar to the personal shopping parameters for one or more users.

In another variant, individual content objects (such as video, text, audio, images, etc.) are tagged and stored, then accessed by the server and/or user device for the generation of targeted pages as discussed herein. According to this embodiment, a single page may be built of individual tagged objects in a manner similar to that discussed elsewhere herein.

A second content page may include the tags "golf" and "Jordan Spieth" to indicate that the content page is associated with an entire line of products endorsed by the professional golfer, Jordan Spieth. The line of products may include any number of different products such as golf cleats, golf pants, golf shirts, golf hats, running shoes, training shirts, etc. Users having personal shopping parameters that match the content page tags may be presented with this targeted content page. As yet another example, a third content page may include the tags "basketball" and "shoes" and "Steph Curry" to indicate that the content page is associated with the so-called "Curry One" or "Curry Two" basketball shoe sold by Assignee hereof, as well as an entire line of products endorsed by the professional basketball player, Steph Curry. The line of products may include any number of different products such as socks, shorts, shirts, hats, balls, etc. Again, users having personal shopping parameters that match the content page tags may be presented with this targeted content page. As explained in further detail below, each of the targeted content pages 325 includes purchase options for the user, such as one or more links to a product sales page that allows a user to select options (e.g., size, color, style, etc.) for a product presented on the targeted content page and purchase such product.

The operational records 326 include current and historical data stored by the system server 300 in association with operation of the system server 300, execution of the health tracking program 318, and manipulation of data 320 within the memory 306. For example, the operational records 326 may include information concerning amendments made to any of various activity logs 332. The operational records 326 may also include other information related to the control and operation of the system server 300, including statistical, logging, licensing, and historical information.

As noted previously, the graphics 328 are configured to be displayed as various graphical views on the health tracking device (such as the smartphone 200, laptop 230 and/or desktop computer 240). In one embodiment, graphical views 328 are provided at the server 300 which are pushed to the health tracking device for display thereat as various screen arrangements when the health tracking application 218 and/or the sales application 219 is in use. The graphics 328 may include one or more photos, drawings, illustrations or other graphical material that is used in association with the targeted content pages 325. Examples of such screens for display on a health tracking device are provided in FIGS. 5-12, discussed in further detail below.

While the system server 300 has been explained in the foregoing embodiment as housing each of the instructions 316 and the data 320 in the memory 306, it will be recognized that these components may be retained in other one or more different locations within the health tracking system 100, and may be in remote communication with one another. For example, in at least one embodiment, the health tracking program 318 is retained at a first server while the sales program 319 is retained at a second server. As yet another example, the targeted content pages 325 may be retained at data store location that is separate from the memory 306 of the server 300 where the user data 322 is stored. Moreover, data processing responsibilities may be shared between two different processors at two different locations. For example, some of the data processing and/or storage for the health tracking program 318 and/or the sales program 319 may be shared with one or more remote computers. In such embodiments, the health tracking program 318 and the sales program 319 may utilize any number of APIs to access the data in the third party databases and incorporate such information for use in the health tracking program 318 and the sales program 319. Accordingly, it will be recognized that the description of the system server 300 of FIG. 3 is but one exemplary embodiment of a data processing system that may be utilized by the health tracking system 100.

Method of Providing Targeted Content Pages Based on Health Data

Methods 400 for providing targeted content pages based on information obtained from the health parameter tracking system 100 are described below. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 304 of the system server 300 and/or the processor 208 of the smartphone 200 may function as such a controller or processor. Alternatively, the controller can be implemented with more than one processor and associated circuitry and components, each of which is configured to form one or more tasks or functions described herein. Additionally, the steps of the methods may be performed in any feasible order, regardless of the order shown in the figures or the order in which the steps are described.

The method 400 of FIG. 4 begins in step 410 with obtaining user profile data for a user of the health tracking system 100. As noted previously, the user profile data identifies the user and various user demographics within the health tracking system 100. The user profile data may include, e.g., user gender, height, weight, user identifier, password, normalized vital statistics, health conditions of the user, favorite or preferred sports, favorite or preferred athletes, etc. As shown in the embodiment of FIG. 3, the user profile data may be stored in the profiles 330 of the data 320 in the memory 306. Accordingly, the user profile data may simply be obtained from the server 300 for existing users of the health tracking system 100. In other embodiments, the user profile data may be obtained in a different manner, such as receiving the user profile data from a remote location or receiving and storing user profile data entered directly by the user.

With continued reference to FIG. 4, after the user profile data is obtained in step 410, the method continues in step 420 by receiving user health data from a health tracking device. The user health data may be obtained by the health tracking device using a sensor. Alternatively, the user health data may be manually entered by the user in to the health tracking device. As noted previously, examples of user health data include steps taken, stairs climbed, time slept, distance travelled, heart rate, calories consumed, food consumed, water intake, calories spent, breathing rate, and any of various other metrics.

After the health data is received from the health tracking device in step 420, the method continues in step 430 by determining personal shopping parameters for a user. The personal shopping parameters for the user are aspects relating to the user which are determined based at least in part on both the user profile data and dynamically updated health parameter or activity data relating to the user. An algorithm, content management system or other tool may be used to methodically determine the personal shopping parameters for the user based on the user profile data and the user health data. For example, the algorithm may select certain user profile data (e.g., user gender, user weight, user preferences, etc.) for the personal shopping parameters and process the user health data (e.g., an activity type recently experienced by the user, distance run over a period of time, user heart rate, time logged in a gym, etc.) to determine other personal shopping parameters. In at least one embodiment, the personal shopping parameters may be provided as a set of personal tags associated with the user. The personal shopping parameters may be included as part of the user data 322, such as part of the user profile, or may be stored in a separate database.

The personal shopping parameters may be the same as or overlap with a set of product facets associated with the product records. The personal shopping parameters may be derived from various sources, and particularly from the user data 322 including the user profile data and the user health data. For example, for one user, the personal shopping parameters may include the following: "female," "running," "shoes," "skiing," and "Lindsey Vonn." In this example, the personal shopping parameters of "female," "skiing" and "Lindsey Vonn" may all be derived from answers to onboarding questions received from the user and stored in the user profile. These onboarding questions may be presented to the user at any number of different times, such as when creating the user profile data in the health tracking system 100, or upon downloading or opening the health tracking application 218 or the sales application 219 on the health tracking device. On the other hand, the personal shopping parameters "running" and "shoes" may be derived from recent health data provided by the health tracking system 100. For example, the health data in the activity logs 332 may indicate that the user has recently run over 100 miles (or participated in some other significant running activity) and could therefore be interested in purchasing products related to running (e.g., shoes, socks, shorts, and other gear).

With continued reference to FIG. 4, in step 440 a plurality of targeted content pages are prepared. While step 440 has been shown in the method 400 as occurring after step 430, it will be recognized that the step may occur in a different order within the method, such as before any of steps 410, 420 or 430. As noted previously, each of the targeted content pages 325 is associated with a plurality of content page tags that associate the targeted content page with one or more personal shopping parameters and/or product facets. This association may be based at least in part on the similarity of the content page tags with various personal shopping parameters and/or product facets. Furthermore, each of the plurality of targeted content pages is associated with at least one product, or a set of products, and includes links to other content pages such as a product sales page that allows the user to purchase one or more products presented on the content page. In one embodiment, the association of products to tags is performed via a network operator upon introduction of each product for sale. The associations may be adjusted or honed over time, such as via a feedback mechanism. That is, when a tag is applied to a product, the frequency with which the product is selected for viewing and/or purchase by a consumer is used to determine whether the tag was appropriate. In some embodiments, subsequently derived more specific categories may be added over time. For example, a particular item of yoga gear may be viewed or purchased above a threshold rate by users whose activity data would classify them as high frequency runners. Accordingly, the yoga gear may subsequently be tagged as appropriate for display to runners as well. This system may be include further granularity, such as to categorize the level of runner (such as based on the frequency of running activity, distance run in each workout, etc.) in order to match the subsequently created categories (e.g., high frequency runners, long distance runners, etc.).

A content management system may be provided as part of the health tracking system 100 and used to prepare the content for the targeted content pages, the content including information from at least one product record. The content management system may be used to prepare content for any number of different targeted content pages, with each targeted content page having a unique combination of content page tags.

In at least one embodiment, the targeted content pages are prepared as narrative content pages. In this embodiment, each of the plurality of targeted content pages includes a narrative portion and a product portion. The narrative portion provides a story, report or account of connected events, experiences, or the like presented in a sequence of words, sounds or images. Therefore, the narrative portion may be directed to a person, a sport, a sporting event, a product or a product line, a shopping event, or any of various other topics of interest. For example, the narrative portion may provide a story of an athlete experience, a description of a manufacturing process, an upcoming or past event of historical or other significance, a description of a sales event, or any number of other reports or accounts of connected events. The narrative portion may be provided using any of various types of media, including text, audio, video or other media.

The product portion of the narrative content page provides a description of a product offered for sale. The description of the product includes basic factual information about the product offered for sale that is not in narrative form, and this distinguishes the product portion of the narrative content page from the narrative portion. The product portion may be provided in any of various formats, such as a full description of the product, or a link to another content page where the product is described in further detail. The product portion may be included within the narrative portion (e.g., the product portion may be a link within the narrative portion) or may be completely separate from the narrative portion (e.g., the product portion may be included before or after the narrative portion). When included in the narrative portion, a product itself is part of the narrative. For example, a product may be described in the narrative portion as being instrumental to an athletic performance. As another example, a technology used for various products may be described in the narrative portion. In these instances, a link to a product sales page may be provided directly in the narrative portion to a product description page and/or a sales page demonstrating all of the products that use the technology. Alternatively, if the narrative portion of the targeted content page does not specifically involve one or more products, links to the product description page and/or the product sales page may be provided after or before the narrative portion.

After the plurality of targeted content pages are prepared in step 440, the method continues with step 450 and one or more of the plurality of targeted content pages is selected for presentation to the user on the health tracking device. The selected targeted content page is based at least in part on the personal shopping parameters for the user and the similarity of such personal shopping parameters to the plurality of content page tags for each of the plurality of targeted content pages. For example, the content management system may index all of the targeted content pages and the content page tags that have been applied to those targeted content pages, and then compare the user's personal shopping parameters to the indexed content page tags in order to determine targeted content pages are most relevant to the user. Accordingly, in at least one embodiment, the selected targeted content page is the content page having a set of content page tags that most closely matches the personal shopping parameters of the user. Alternatively, a number of targeted content pages may be selected and presented to the user based on a minimum threshold association between the user's personal shopping parameters and the content page tags. For example, in the previously noted example where the personal shopping parameters of the user were "female," "running," "shoes," "skiing," and "Lindsey Vonn," the system may select a first targeted content page having the tags "female," "running," and "shoes," (but not "skiing" and "Lindsey Vonn"), and a second targeted content page having the content page tags "female," "skiing," and "Lindsey Vonn" (but not "running" and "shoes"). Accordingly, it will be recognized that one or more targeted content pages may be presented to the user based on some threshold association between the personal shopping parameters of the user and the content page tags (e.g., a perfect match or simply a minimum number of matches).

Selection of one or more targeted content pages for presentation to the user may occur based on any number of different triggers when the user is using the health tracking application 218 or the sales application 219. In at least one embodiment, one or more targeted content pages are the first content pages presented to the user when the user starts the sales application 219 or the health tracking application 218. However, in at least one alternative embodiment, one or more targeted content pages are presented to the user via the health tracking application 218 upon completion of a workout, or upon some other trigger. Examples of other triggers that may result in presentation of targeted content pages to the user include the user logging a predetermined number of running miles, or trying a new activity for the first time, etc. Whether the targeted content pages are presented to the user when running the health tracking application 218 or the sales application 219, the targeted content pages provide one or more links to content pages in the sales application 219 that allow the user to make product selections and purchases. If the user is not interested in the targeted content page, a menu option is provided to allow the user to visit different content pages within the site.

In another embodiment, the personal parameters and/or selection of targeted pages may utilize a recommendation engine such as that discussed in co-owned, co-pending U.S. patent application Ser. No. 15/086,476; filed on Mar. 31, 2016; entitled "Methods and Apparatus for Enhanced Product Recommendations"; and incorporated herein by reference in its entirety. As discussed therein, a recommendation engine may be provided which is configured to compare a plurality of product profiles (and/or targeted content pages relating thereto) to a profile of the user. As noted above, the user profiles may be created from user-specific information as well as health parameter data obtained from the heath monitoring devices. In another embodiment, each user may be associated to a static profile and a dynamic profile (as discussed in the previously referenced U.S. Patent Application). The user and product profiles are updated such as in response to newly collected activity and profile data as discussed therein.

The recommendation engine performs a comparison of a specific consumer's user profile(s) to each of the available product profiles. In one exemplary embodiment, this is performed via one or more of: (i) filtering in/out product profiles based on the consumer's static aspects; (ii) calculation of a scalar quantity via a dot product of a user dynamic profile vector and each of the filtered product profile vectors; (iii) comparison of the calculated scalar quantities to a threshold; and/or (iv) performing the calculations associated with the previously described score modules. Those ones of the product records which have a scalar quantity or an overall score at or above a given threshold are then provided as targeted content pages to the user device and/or the device is instructed to place the content pages relating to the identified products into a targeted content page.

The methods discussed herein may be accomplished with the assistance of a computer program, such as the client side health tracking application 218, the network side health tracking program 318, and the network side sales program 319 described above. The above described system and method solves a technological problem common in industry practice related to effective and efficient presentation of product data to users of a health tracking system 100. Moreover, the above-described system and method improves the functioning of the computer/device by allowing health data to be effectively communicated to the user along with a graphical user interface that presents purchase options to the user that are associated with the user's health data.

Exemplary Targeted Content Page

With reference now to FIGS. 5-8, an exemplary targeted content page 500 is shown displayed on a user's smartphone 200. The targeted content page 500 has been deemed to be relevant (or targeted) to the particular user based on the user's personal shopping parameters, health parameter data, and/or other data collected relating to the user, which are matched to the content page tags associated with the targeted content page 500. The exemplary targeted content page 500 of FIGS. 5-8 is configured with a number of content screens, with each of the content screens arranged on the content page 500 for sequential display on the smartphone 200 in this example as the user scrolls through the content page 500. Each content screen includes an upper content portion 504 and a lower menu portion 506. As noted previously, the targeted content page 500 may be provided in association with either (i) the health tracking application 218 (and the associated health tracking program 318 at the network-side), and/or (ii) the sales application 219 (and the associated sales program 319 at the network-side).

Figure 5:
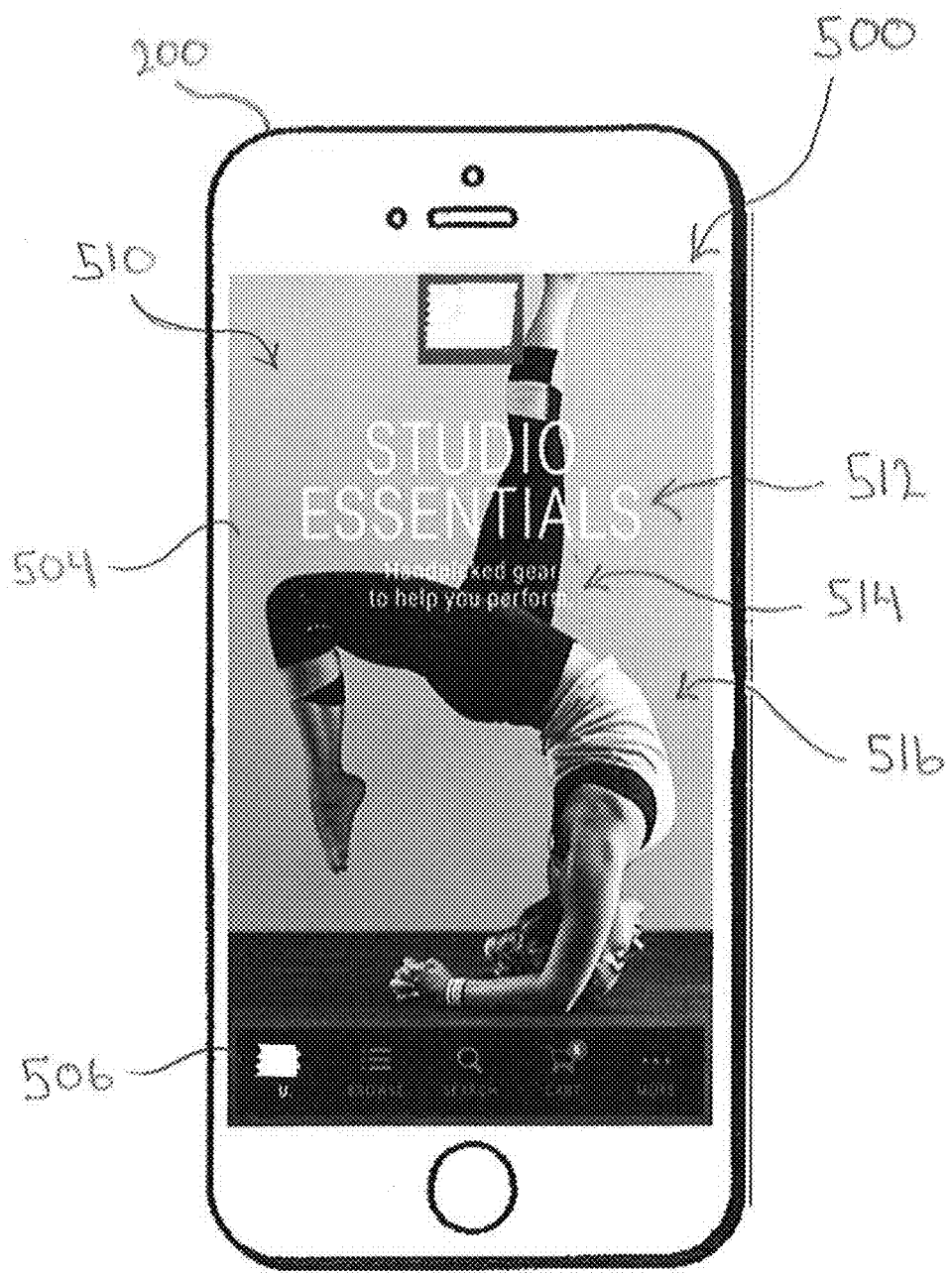
FIG. 5 is a representation of a first content screen of an exemplary targeted content page of the health tracking system of FIG. 1.

A first content screen 510 of the exemplary targeted content page 500 is shown in FIG. 5. The upper content portion 504 of the first screen 520 provides an introduction to the content page 500, informing the user of the content provided on the content page 500. In the embodiment of FIG. 5, the upper content portion 504 includes a title 512 (i.e., "Studio Essentials"), a content page description 514 (i.e., "Handpicked gear to help you perform."), and a photo 516 of an athlete performing a sport that is associated with the content page (i.e., the athlete in the photo of FIG. 5 is in a training pose for dance). Together, the title 512, content page description 514, and photo 516 are designed to introduce the user to the general topic of the targeted content page 500 while also providing content intended to capture the interest to the user such that he or she will continue to scroll through the content page.

As noted previously, the targeted content page 500 is associated with a plurality of content page tags, and each of these content page tags is the same as, similar to, and/or associated with one or more of the personal shopping parameters (which may also be the same as or similar to one of the product facets). In this manner, the targeted content page 500 is configured for presentation to a user who is likely to be interested in at least one product associated with the targeted content page. In the embodiment of FIGS. 5-8, the content page tags for the targeted content page 500 may include one or more of the following: "dance," "ballet," "yoga," "training gear," "female," "Misty Copeland," "tops," "pants," "bra," and/or any number of additional content page tags. The network operator may set a minimum number of personal shopping parameters which must match those of the targeted content page 500 (e.g., three or more matches such as "dance," "female," and "training gear") in order for the targeted content page 500 to be selected by the health tracking system 100 for presentation to the user and then subsequently displayed on the user's smartphone 200 or other device.

After viewing the first page 510 of the targeted content page 500, the user may choose to continue scrolling through the available content screens of the targeted content page 500 or exit the targeted content page 500 by selecting an option from the menu 506. If the user wishes to scroll through the content screens of the targeted content page, in one embodiment, the user slides his or her finger across the display screen of the smartphone 200 (e.g., swipe), the user will be presented with another content screen. Alternatively, the user may scroll down, or select a new screen using a touch screen icon, or the like.

Figure 6:
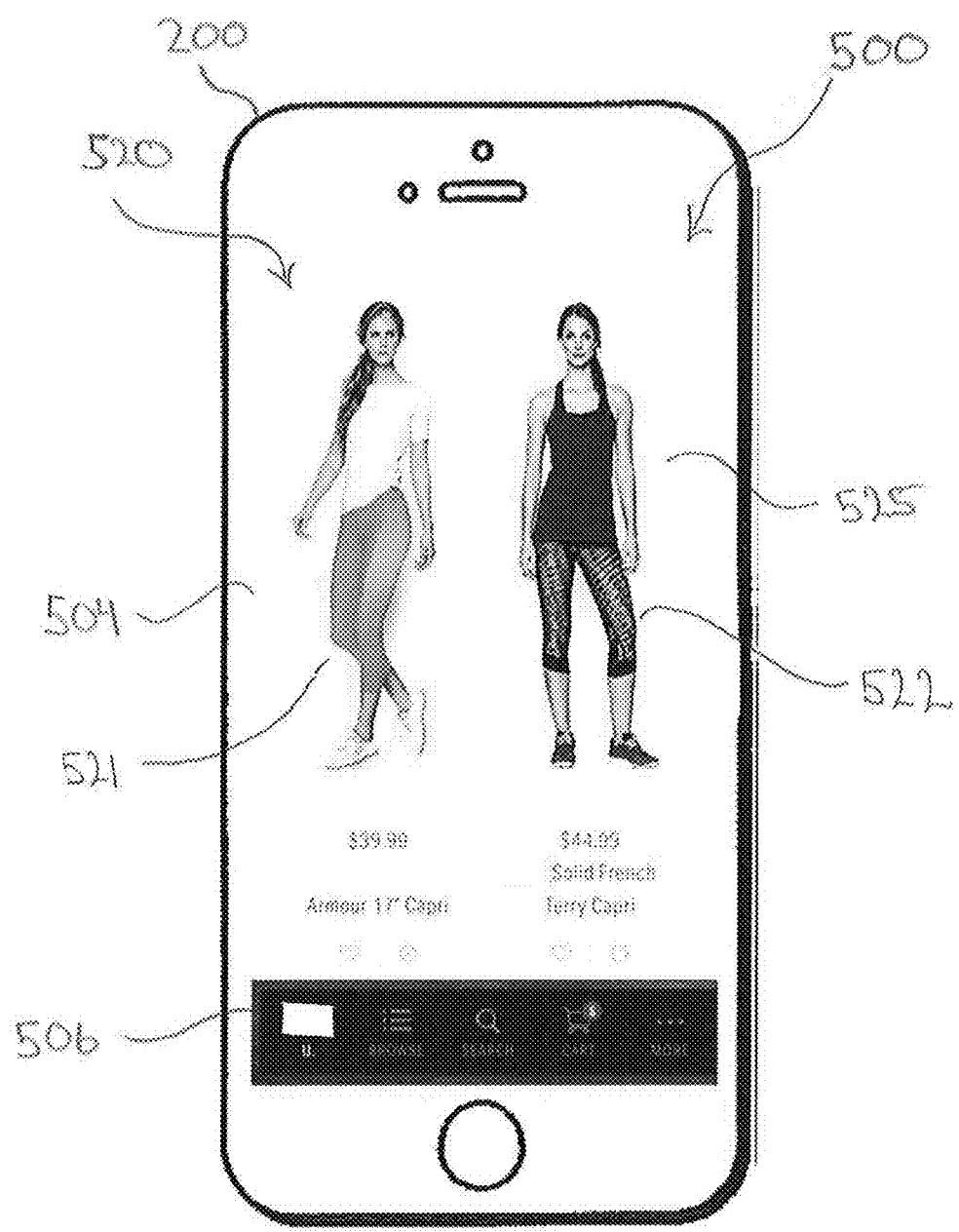
FIG. 6 is a representation of a second content screen of the exemplary targeted content page of the health tracking system of FIG. 1 providing a first product portion.

FIG. 6 shows the second content screen 520 of the targeted content page 500. The second content screen 520 provides a first product portion 525 of the targeted content page 500 which presents several products offered for sale via the targeted content page 500. The products offered for sale include a first capri pant 521, and a second capri pant 522. Product data 324 for both the first capri pant 521 and the second capri pant 522 (as well as other available products) is stored at the network-side server or other entity in communication therewith. Information concerning the first capri pant 521 and the second capri pant 522 is presented to the user on the second content screen 520. In the embodiment of FIG. 6, the information includes a product photo, product price and product name for each of the first capri pant 521 and the second capri pant 522. If the user selects either of the first capri pant 521 or the second capri pant 522

(e.g., by clicking on the product with a mouse, scrolling to a portion of the page with further details, and/or touching the product information tab on the screen), the user is forwarded, via a link, to a product sales page that allows the user to select size, color and related options for the selected product, save the product to his or her shopping cart, and then purchase the saved product. In this manner, the first product portion 525 provides purchase options to the user within the targeted content page 500.

Figure 7:
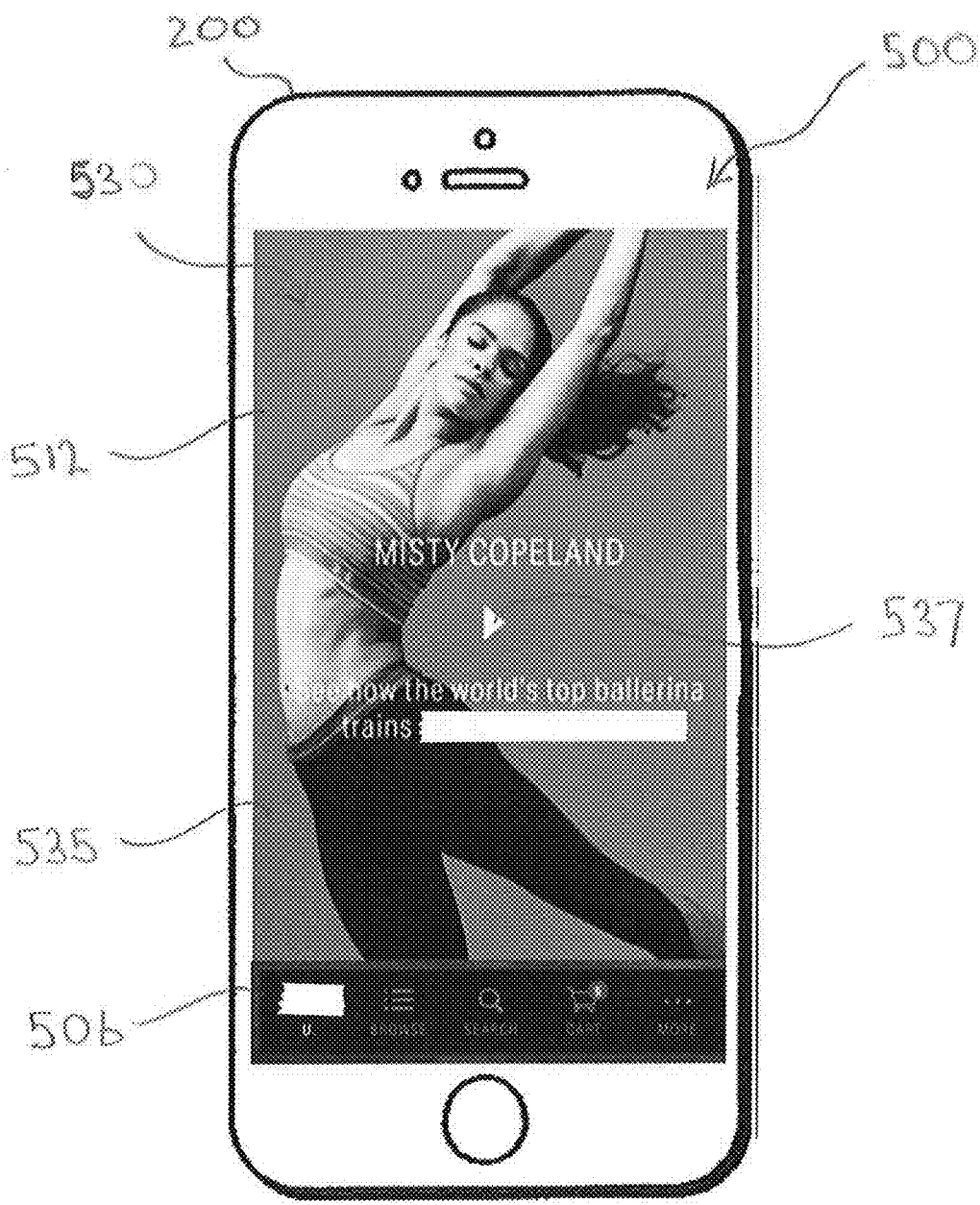
FIG. 7 is a representation of a third content screen of the exemplary targeted content page of the health tracking system of FIG. 1 providing a narrative portion.

FIG. 7 shows the third content screen 530 of the targeted content page 500. The third content screen 530 provides a narrative portion 535 of the targeted content page 500. In the embodiment of FIG. 7, the narrative portion 535 of the targeted content page 500 is directed to the experience of Misty Copeland in the sport of dancing, and particularly ballet, along with related training activities and products offered for sale. The narrative portion 535 includes a media file that includes audio and video providing an account of Misty Copeland's training activity. By selecting the play option 537, the user may play the medial file and view and hear the media file. The account of Misty Copeland's training activity may include a description of her daily training routine, training tips, useful products for effective training, and/or an inspirational message. The account may also include one or more references to products used by Misty Copeland during her training activities. A link to a sales page that allows the user to purchase such products may be shown on the same screen as the narrative portion 535 (e.g., directly on screen 530 of FIG. 7) or may be provided on one or more separate screens (e.g., screens 520 of FIG. 6 or screen 540 of FIG. 8).

It will be recognized that although the narrative portion 535 of the targeted content page 500 in FIG. 7 provides an account of Misty Copeland's training experience for ballet, various other accounts of connected events may be provided in alternative embodiments of the content page 500. For example, in other embodiments, the narrative portion of the targeted content page may describe a manufacturing process, features of a particular technology used in the product, an upcoming or past event of historical or other significance (including e.g., holidays, sales, upcoming events the user may join such as races, etc.), a description of a sales event, or any number of other reports or accounts of connected events. Additionally, although the narrative portion 535 of the content page 500 of FIG. 7 has been described as a media file including video and audio, the narrative portion may be provided in various other forms, such as drawings, illustrations, text and/or other media.

Figure 8:
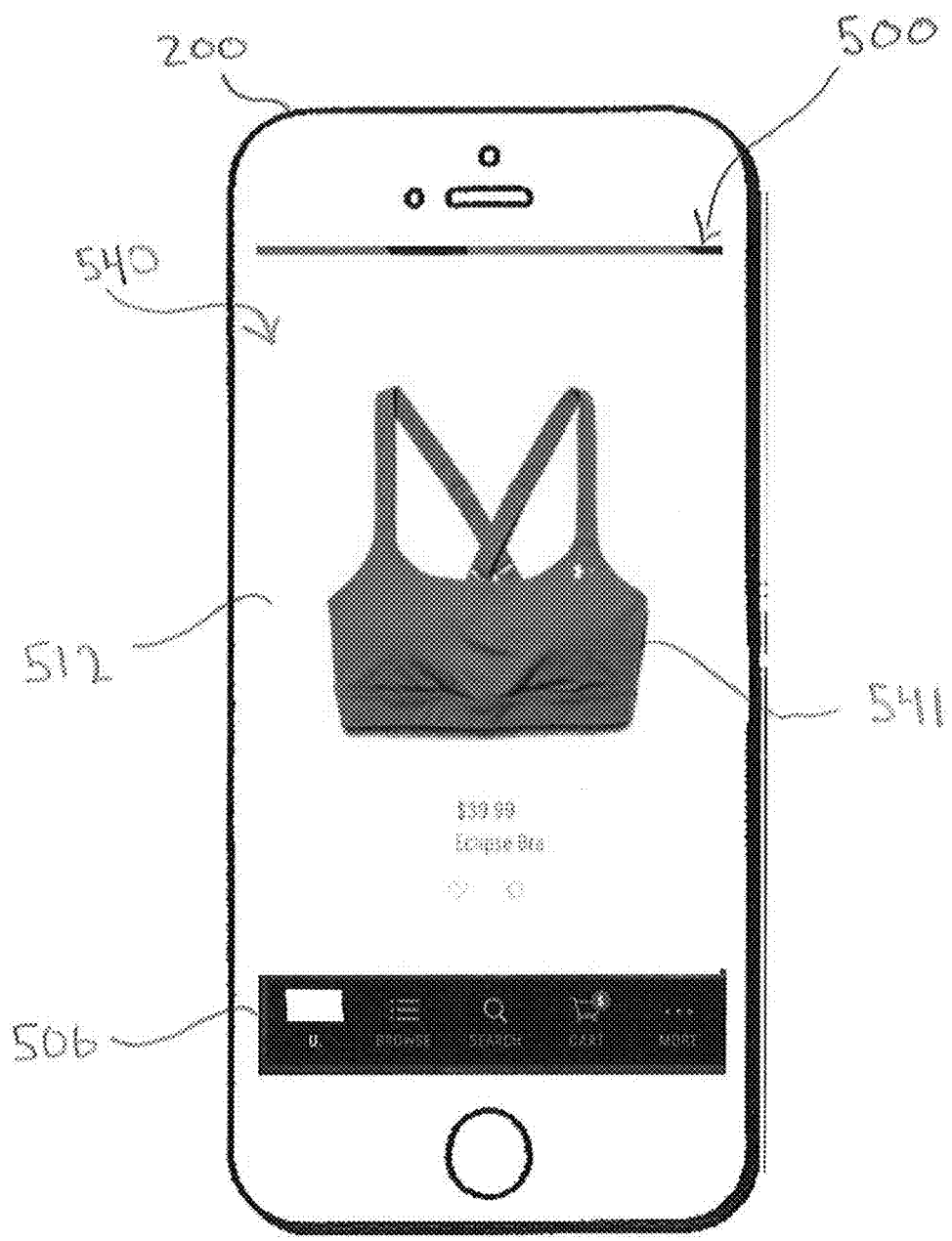
FIG. 8 is a representation of a fourth content screen of the exemplary targeted content page of the health tracking system of FIG. 1 providing a second product portion.

FIG. 8 shows the fourth content screen 540 of the targeted content page 500. The fourth content screen 540 provides a second product portion 545 of the targeted content page 500 presenting details relating to a single product offered for sale via the targeted content page 500. The product offered for sale on the fourth content screen 540 is a sports bra 541. Product data 324 for the sports bra 541 is included in the data 320 of the health tracking system 100. Information concerning the sports bra 541 is presented to the user on the fourth content screen 540. In the embodiment of FIG. 8, the information includes a product photo, product price and product name for the sports bra 541. If the user selects the sports bra 541, the user selects a link to a product sales page that allows the user to select size, color and related options for the selected product, save the product to his or her shopping cart, and then purchase the saved product. In one embodiment, the user is linked to this detailed content page 540 when he/she clicks on the product in another content screen (e.g., by clicking the item demonstrated in the images at FIG. 6). In another embodiment, the user is provided with this detailed content page 540 when he/she scrolls down from any of the previously discussed content pages. In other words, the user may receive further details via a detailed content page 540 about each of the products given in a screen which displays multiple products such as that of FIG. 6.

Figure 9:
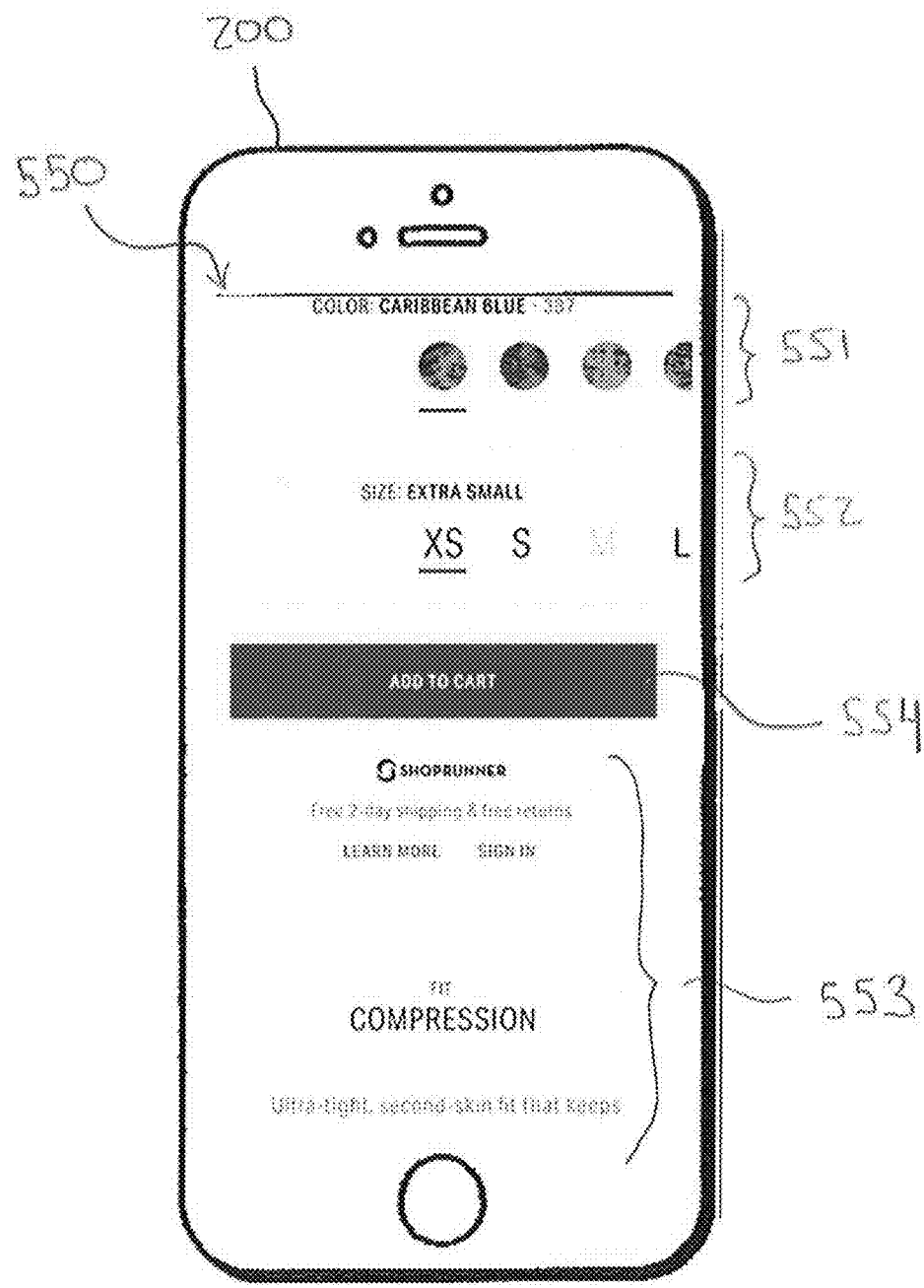
FIG. 9 is a representation of an exemplary product sales page of the exemplary targeted content page of the health tracking system of FIG. 1.

With reference now to FIG. 9, a product sales page 550 is shown. The product sales page 550 is typically presented as a content page provided by the sales application 219 after the user selects a link associated with a product on the targeted content page. In the embodiment of FIG. 9, the user selected the link associated with the sports bra 541 on the fourth screen 540 of the targeted content page 500, and is presented with the product sales page 550. The product sales page 550 presents the user with a number of selectable product options for the desired product for purchase. For example, the product sales page 550 includes a product color selection 551 and a product size selection 552. The product sales page 550 may also include additional information about the product or the sale of the product. For example, in the embodiment of FIG. 9, the product sales page 550 includes an additional information section 553 that provides information concerning shipping of the product, the type of fabric, and other product information. Although not illustrated, various images of the product having the specific colors, etc. selected by the user may be displayed as well. After the user has reviewed the information section 553 and made the appropriate product selections, the user may choose to place the product in his or her shopping cart by selecting the cart option 554. The user may then visit the shopping cart and provide payment information in order to purchase the product, or may continue shopping.

As noted previously, if the user wishes to leave the targeted content page 500 at any time, the user may select one of the options on the menu 506. As shown in FIGS. 5-8, the menu options include a targeted content pages option 562, a browse option 564, a search option 566, a shopping cart option 568, and additional options 570. By selecting the targeted content page option 562, the user is presented with other targeted content pages that may be of interest to the user based on the user's personal shopping parameters. By selecting the browse option 564, the user is presented with various categories and sub-categories of topics available for sale (e.g., "women's running shoes" or "golf apparel"). By selecting the search option 566, the user is presented with a search box that allows the user to search for particular products available for sale (e.g., "men's hiking boots") which might not have been provided as targeted items to that user. By selecting the shopping cart option 568, the user is presented with a cart of saved items that are ready to purchase. By selecting the additional options 570, the user is presented with various additional options (e.g., change profile, log off, settings, etc.).

Figure 10:
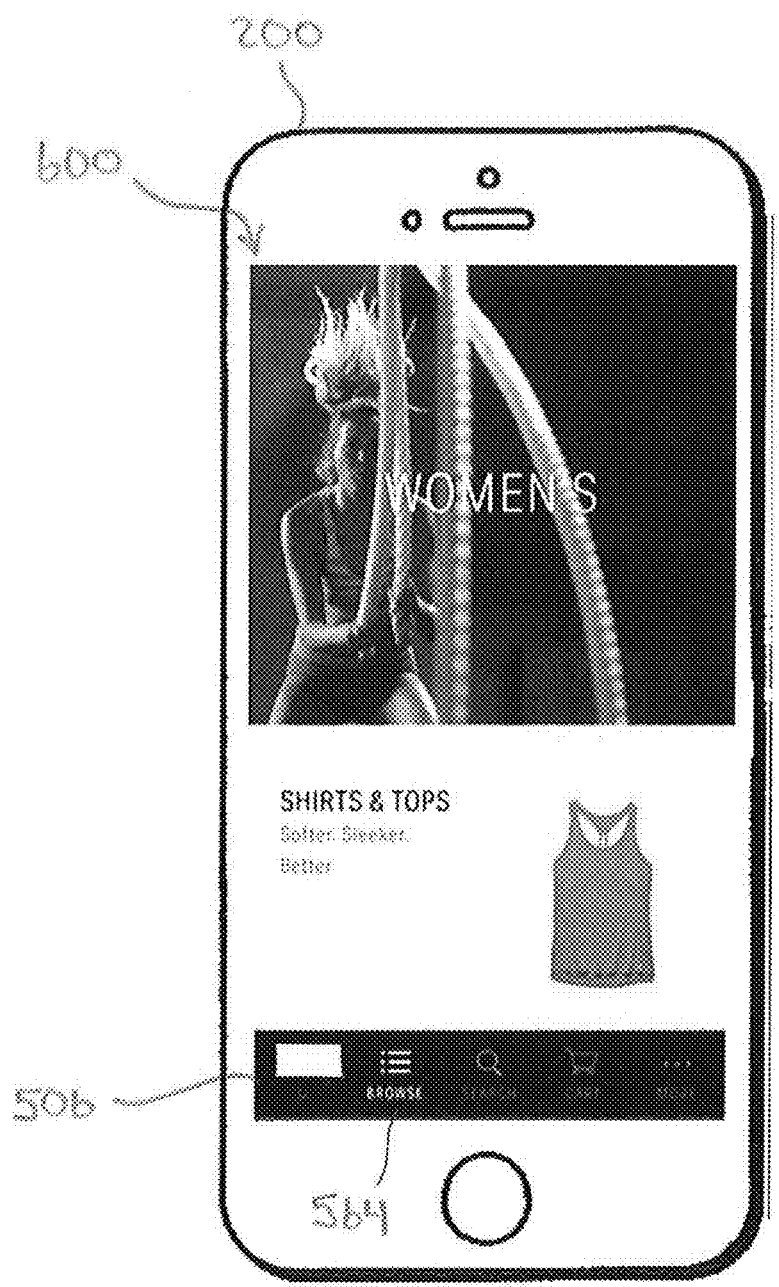
FIG. 10 is a representation of an exemplary browsing page of the exemplary targeted content page of the health tracking system of FIG. 1.

FIG. 10 shows an exemplary embodiment of a browsing content page 600 that may be presented to the user after the user selects the browse option 564 from the menu 506. In this example, the user has selected to browse for women's shirts and tops. After selecting the "shirts and tops" option, the user may be presented with additional sub-categories for selection within the topic (e.g., "yoga," "running," "basketball," etc.). After making appropriate selections, the user may simply scroll through all of the available products within the sub-category.

Figure 11:
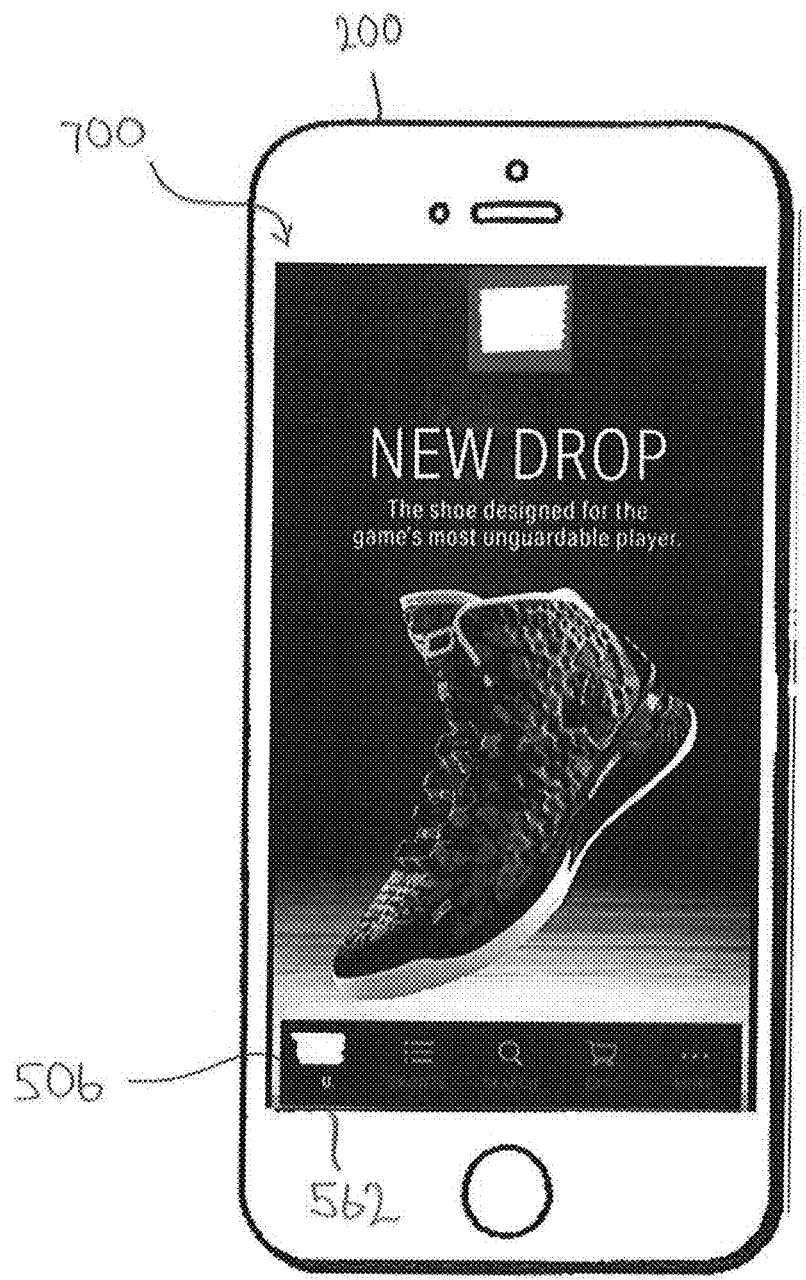
FIG. 11 is a representation of another exemplary targeted content page of the health tracking system of FIG. 1.

FIG. 11 shows another exemplary embodiment of a targeted content page 700. The content page 700 may be presented to the user after the user selects the targeted content page option 562 from the menu 506, in conjunction with the methods discussed above for providing targeted pages, and/or upon a user browsing or search. In the exemplary embodiment of FIG. 11, the targeted content page 700 includes content related to a basketball shoe endorsed by a famous athlete. The targeted content page 700 is directed to those users who play or are interested in basketball. The targeted content page 700 includes a number of content page tags such as "basketball," "shoe," and "Steph Curry". Because the personal shopping parameters of the user match some number of the content page tags, the targeted content page 700 of FIG. 11 is presented to the user when the targeted content page option 562 is selected. The targeted content page 700 includes both a narrative portion (not shown) and a product portion (not shown). As discussed previously, the narrative portion provides a story, report or account of connected events, experiences, or the like presented in a sequence of words, sounds or images. In another alternative the targeted content page 700 may be accessed via a general browsing or searching feature (as discussed above). In the embodiment of FIG. 11, the narrative portion of the targeted content page 700 may be directed to Steph Curry's shooting performances during the 2015-2016 National Basketball Association season, and the shoes he was wearing during such shooting performances. The narrative portion may be provided using any of various types of media, including text, audio, video or other media. The product portion of the targeted content page 700 provides a description of a product offered for sale via the health tracking system 100, such as the Steph Curry basketball shoe. The description of the product includes basic factual information about the product offered for sale that is not in narrative form, and this distinguishes the product portion of the narrative content page from the narrative portion. The product portion may be provided in any of various formats, such as a full description of the product, or a link to another content page where the product is described in further detail. As noted previously, the product portion may be included within the narrative portion (e.g., the product portion may be a link within the narrative portion) or may be completely separate from the narrative portion (e.g., the product portion may be included before or after the narrative portion).

Figure 12:
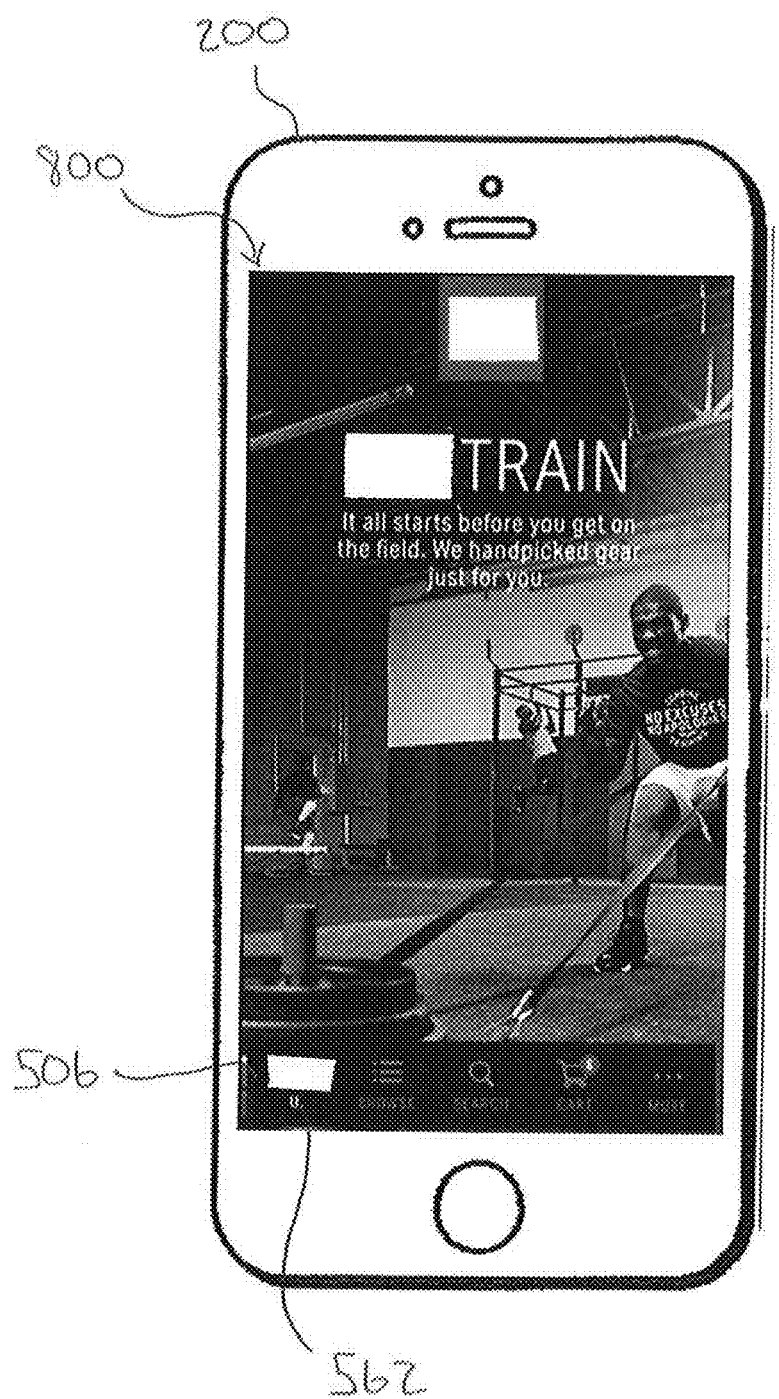
FIG. 12 is a representation of a third exemplary targeted content page of the health tracking system of FIG. 1.

FIG. 12 shows another exemplary embodiment of a targeted content page 800. The content page 800 may be presented to the user after the user selects the targeted content page option 562 from the menu 506, in conjunction with the methods discussed above for providing targeted pages, and/or upon a user browsing or search. In the exemplary embodiment of FIG. 12, the targeted content page 700 includes content related to cross-training. The targeted content page is directed to those users who record significant amounts of time participating in a "cross-training," "weightlifting" or "gym" activity type. The targeted content page 800 includes a number of content page tags such as "training," "men's," "shoes," "shirts," "bottoms," and "equipment". Because the personal shopping parameters of the user match some number of the content page tags, the targeted content page 800 is presented to the user when the targeted content page option 562 is selected. For example, if the user is a male who has logged one hundred hours of gym workouts in a year using the health tracking system 100, the user's personal shopping parameters may result in a sufficient match the content page tags of the targeted content page 800 such that it is selected by the system 100 as one of the targeted content pages for the user. If system 100 selects five targeted content pages for the user, each of these may be provided automatically and presented as a scroll-able or swipe-able list. Alternatively, a new targeted content page may be presented with each subsequent pressing of the targeted content page option 562. The targeted content page includes both a narrative portion (not shown) and a product portion (not shown). The narrative portion provides a story, report or account of connected events, experiences, or the like presented in a sequence of words, sounds or images. In the embodiment of FIG. 12, the narrative portion of the targeted content page 800 may be directed to a unique sales event related to training equipment, the rules associated with the sales event, and special opportunities offered during the sales event (e.g., random drawings, recognitions, etc.). The narrative portion may be provided using any of various types of media, including text, audio, video or other media. The product portion of the targeted content page 800 provides a description of various products offered for sale, such as training shoes, training garments, and training equipment. The descriptions of the various product include basic factual information about each product offered for sale. The product portion may be provided in any of various formats, such as a full description of the product, or a link to another content page where the product is described in further detail.

The methods discussed herein may be accomplished with the assistance of a computer program, such as the network and/or client side health tracking applications and sales applications described above. The above described system and method solves a technological problem common in industry practice related to effective and efficient presentation of product information to the user. Moreover, the above-described system and method improves the functioning of the computer/device by utilizing health parameter and activity data to dynamically provide targeted content pages and by allowing product data to be effectively communicated to the user along with a graphical user interface that presents product purchase options to the user in association with personal shopping parameters of the user.

In one embodiment, a method of operating a health tracking system is disclosed. In one variant, the method comprises: (i) obtaining user profile data for a user; (ii) receiving health parameter data from a health tracking device, the health parameter data obtained by a sensor and/or manually entered by the user; (iii) determining one or more personal shopping parameters for a user based at least in part on the user profile data and the health parameter data; (iv) selecting at least one of a plurality of targeted content pages, each of the plurality of targeted content pages associated with one or more descriptive tags, wherein selecting at least one of the plurality of targeted content pages is based at least in part on the one or more personal shopping parameters for the user and the one or more descriptive tags associated with each of the plurality of targeted content pages; and (v) providing the selected at least one of the plurality of targeted content pages to a display device.

In another variant, the method comprises: (i) generating a user profile comprising data relating to a user; (ii) receiving health parameter data from a health tracking device, the health parameter data obtained by a sensor and/or manually entered by the user; (iii) determining one or more aspects relating to the user based at least in part on the health parameter data; (iv) selecting one or more content objects relating to purchasable items for the user based on the determined one or more aspects relating to the user; and (v) enabling the selected one or more content options to be provided to a user display device.

In another embodiment, a method of presenting products for purchase on a display device is given. The method comprises: (i) determining one or more user specific parameters; (ii) selecting at least one of a plurality of targeted content pages, each of the plurality of targeted content pages including a narrative portion and a product portion, and each of the plurality of targeted content pages being associated with one or more descriptive identifiers based at least in part on a similarity between the one or more user specific parameters and the one or more descriptive identifiers associated with each of the plurality of targeted content pages; and (iii) sending the selected at least one of the plurality of targeted content pages to the display device.

Portions of the system and methods described herein may be implemented using one or more programs or suitable software code, such as the network and/or client-side health tracking applications, described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transient computer-readable medium" may be any type of data storage medium that can store computer instructions, including, but not limited to the memory devices discussed above.

The above described system and method solves a technological problem common in industry practice related to effective and efficient presentation of product data to a user for analysis and consideration by the user. Moreover, the above-described system and method improves the functioning of the computer device by causing product data to be easily presented to a user in association with a health tracking system, thus also allowing the user to easily learn about and purchase various products that are likely to be of interest to the user. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system comprising:
   at a server, obtaining user profile data for a user transmitted from a health tracking device of the user;
   at the server, obtaining health parameter data from the health tracking device associated with the user, the health parameter data collected by the health tracking device from a sensor carried by the user, the health parameter data including distance data relating to an running or walking activity in which the user recently participated;
   at the server, determining one or more personal shopping parameters for the user based at least in part on the user profile data and the health parameter data, the personal shopping parameters comprising one or more descriptive tags selected from a plurality of descriptive tags predetermined by a network operator to relate to a plurality of purchasable items sold by the network operator;
   at the server, selecting at least one of a plurality of targeted content pages, each of the plurality of targeted content pages comprising one or more of the purchasable items, the one or more purchasable items being associated with one or more of the plurality of descriptive tags predetermined by the network operator, wherein the act of selecting at least one of the plurality of content pages is triggered when a total distance logged by the user in association with the activity exceeds a distance threshold defined by the network operator, wherein the total distance traversed threshold is a minimum number of miles or kilometers traversed by the user in association with the running or walking activity, and wherein selecting at least one of the plurality of targeted content pages is based at least in part on determining whether a match between the one or more personal shopping parameters for the user and the one or more descriptive tags associated with the one or more purchasable items of each of the plurality of targeted content pages meets a match threshold;
   transmitting the selected at least one of the plurality of targeted content pages from the server to the associated health tracking device and thereby providing the selected content page to a display device of the health tracking device;
   at the server, receiving a selection from the user of the one or more purchasable items included on the selected at least one of the plurality of targeted content pages; and
   at the server, receiving a product order from the user for the one or more purchasable items.

2. The method of claim 1 wherein each of the plurality of targeted content pages includes a narrative portion and a product portion.

3. The method of claim 2 wherein the narrative portion includes text, audio, or video concerning one or more of a person, a sport, an event, a product or a product line.

4. The method of claim 3 wherein the product portion includes at least one product description and at least one link to a product sales page.

5. The method of claim 1 wherein the one or more descriptive tags include one or more of gender, activity type, product type, preferred sport, and preferred athlete.

6. The method of claim 1 wherein the act of determining one or more personal shopping parameters for the user includes using the user profile data and the health parameter data in an algorithm that generates the one or more personal shopping parameters.

7. The method of claim 6 wherein the personal shopping parameters for the user are further based at least in part on answers to questions received from the health tracking device.

8. The method of claim 1 wherein the display device comprises the health tracking device.

9. The method of claim 8 wherein the health tracking device comprises a smartphone and the sensor includes one or more of a heart rate sensor, scale, sleep monitor, and/or step counter.

10. The method of claim 9 wherein the display device is a screen of the smartphone.

11. The method of claim 1 wherein the server sends a request for the health parameter data to the health tracking device.

12. The method of claim 1 wherein the health tracking device periodically transmits the health parameter data to the server.

13. The method of claim 1 wherein the narrative portion further includes one or more links to purchase pages that allow the user to order the one or more of the purchasable items.

14. The method of claim 1 further comprising, after receiving the product order from the user for the one or more purchasable items, amending the descriptive tags associated with the one or more purchasable items based at least in part on the health parameter data of the user.

15. A method of presenting products for purchase from a network operator on a display device and processing orders for such products, the method comprising:
  storing a plurality of product records, each product record describing an individual item for sale by the network operator and comprising one or more of a plurality of descriptive tags;
  determining one or more user specific parameters for a user of a health tracking system, the one or more user specific parameters being represented by individual ones of the plurality of descriptive tags, wherein determining one or more user specific parameters comprises obtaining health parameter or activity data from a health tracking device of the health tracking system associated with the user, the health parameter or activity data collected by a sensor and/or manually entered by the user, wherein the health parameter or activity data includes distance data relating to an a running or walking activity in which the user recently participated, and wherein the network operator is an administrator of the health tracking system;
  determining that the health parameter or activity distance data indicates that the user has performed the activity in which the user recently participated in excess of a total distance traversed threshold defined by the network operator, wherein the total distance traversed threshold is a minimum number of miles or kilometers traversed by the user;
  when it is determined that the user has performed the activity in excess of the total distance traversed threshold, determining one or more personal shopping parameters for the user based at least in part on the user profile data and the health parameter data, the personal shopping parameters comprising one or more descriptive tags selected from a plurality of descriptive tags predetermined by a network operator to relate to a plurality of purchasable items sold by the network operator;
  generating at least one targeted content page based on the determined one or more shopping parameters for the user, the targeted content page comprising individual ones of the plurality of product records having a predetermined number of identical descriptive tags to that of the one or more user specific parameters, the at least one targeted content page further including at least one narrative portion and at least one product portion describing a targeted item for sale associated with at least one of the plurality of product records;
  sending the generated at least one targeted content page to the display device and thereby providing the generated at least one targeted content page to the user for display on the display device;
  receiving a product order from the user for the targeted item for sale; and
  after receiving the product order from the user, amending the descriptive tags of the product record associated with the targeted item for sale based at least in part on the health parameter data of the user.

16. The method of claim 15 wherein the narrative portion includes text, audio, or video concerning one or more of a person, a sport, an event, a product or a product line.

17. The method of claim 16 wherein the product portion includes at least one product description and at least one link to a product sales page.

18. The method of claim 15 wherein the generated at least one targeted content page is associated with at least one descriptive identifier, wherein the at least one descriptive identifier is associated with the one or more user specific parameters, and wherein the one or more descriptive identifiers include one or more of gender, activity type, product type, preferred sport, and/or preferred athlete.

19. The method of claim 15 wherein the display device comprises the health tracking device.

* * * * *